United States Patent
Kovelman

[11] Patent Number: 6,110,152
[45] Date of Patent: Aug. 29, 2000

[54] MEDICATION CARTRIDGE FOR AN ELECTRONIC PEN-TYPE INJECTOR, INFUSION PUMP, ELECTRONIC DELIVERY DEVICE, OR THE LIKE, AND METHOD OF MAKING THE SAME

[75] Inventor: Paul H. Kovelman, Simi Valley, Calif.

[73] Assignee: MiniMed Inc., Sylmar, Calif.

[21] Appl. No.: 09/360,410

[22] Filed: Jul. 23, 1999

Related U.S. Application Data

[63] Continuation-in-part of application No. 09/005,780, Jan. 13, 1998, Pat. No. 5,954,700.

[51] Int. Cl.[7] .................................................. A61M 5/00
[52] U.S. Cl. ........................... 604/232; 604/65; 604/67; 604/189; 604/207
[58] Field of Search .................. 604/65, 67, 181, 604/186, 187, 189, 207–211, 232, 234, 404, 202

[56] References Cited

U.S. PATENT DOCUMENTS

| | | |
|---|---|---|
| 4,573,994 | 3/1986 | Fischell et al. . |
| 4,959,056 | 9/1990 | Dombrowski et al. . |
| 4,978,335 | 12/1990 | Arthur, III . |
| 5,544,651 | 8/1996 | Wilk . |
| 5,545,140 | 8/1996 | Conero et al. . |
| 5,628,309 | 5/1997 | Brown . |
| 5,651,775 | 7/1997 | Walker et al. . |
| 5,681,285 | 10/1997 | Ford et al. . |
| 5,704,922 | 1/1998 | Brown . |
| 5,720,733 | 2/1998 | Brown . |
| 5,782,814 | 7/1998 | Brown et al. . |
| 5,792,117 | 8/1998 | Brown . |

*Primary Examiner*—Wynn Wood Coggins
*Assistant Examiner*—Deborah Blyveis
*Attorney, Agent, or Firm*—MiniMed Inc.

[57] ABSTRACT

A cartridge for containing a fluid and for use with an electronic delivery device, includes a cartridge housing for holding the fluid, and information providing source. The information providing source is coupled to the cartridge housing to operatively couple with the electronic delivery device to provide predetermined information regarding the cartridge to the electronic delivery device. For example, the information providing source may be a set of wires and contacts, or contact bands, that provide the predetermined information to electronic delivery device by producing a binary code. Alternatively, the information providing source is a bar code that provides the predetermined information to electronic delivery device by reading of the bar code. The cartridge may be used in a system that includes an electronic delivery device, such as an electronic pen-type injector and/or infusion pump.

18 Claims, 2 Drawing Sheets

MEDICATION CARTRIDGE FOR AN ELECTRONIC PEN-TYPE INJECTOR, INFUSION PUMP, ELECTRONIC DELIVERY DEVICE, OR THE LIKE, AND METHOD OF MAKING THE SAME

RELATED APPLICATIONS

This is a continuation-in-part of U.S. patent application Ser. No. 09/005,780 filed Jan. 13, 1998, now U.S. Pat. No. 5,954,700 which is herein specifically incorporated by reference.

FIELD OF THE INVENTION

This invention relates to medication cartridges and, in particular embodiments, to a medication cartridge for an electronic pen-type injector, infusion pump, electronic delivery device or the like, that has improved safety and information providing characteristics.

BACKGROUND OF THE INVENTION

Traditionally, medication cartridges have been used with pen-type injectors and are prevalently used worldwide on reusable or multi-dose devices for invasive delivery of medication. However, in typical pen-type injectors, a cartridge is simply inserted into a pen-type injector and used to provide an injection. The pen-type injector does not have any method of determining if the medication cartridge is properly inserted or what type of medication is contained in the medication cartridge. The user must manually check the cartridge for proper insertion and must be sure that the medication is the correct one. This is important, since improper insertion can result in damage to the pen-type injector or in the administration of an incorrect dosage of medication, which could result in injury or death. Also, the user must know what type of medication is being used, since there are often different dosing requirements for different concentrations of the same medication.

To overcome, the proper insertion of the medication cartridge in the pen-type injection, Novo Nordisk developed a plastic cap that mated with matching teeth on the pen-type injector. If the teeth on the plastic cap were not properly lined up and seated in the pen-type injector, the pen-type injector could not be assembled and used. However, this design suffered from several drawbacks, for example, the user could simply force the cartridge into the pen-type injector and force the pen-type injector together by deforming the plastic cap. In addition, the plastic cap could be easily removed.

To overcome the drawbacks concerning what type of medication was contained in the medication cartridge, information was printed on the exterior of the medication cartridge and was viewable through a clear portion on the pen-type injector. However, the user must still view the printing on the cartridge and understand the information presented by the printing.

SUMMARY OF THE DISCLOSURE

It is an object of an embodiment of the present invention to provide an improved medication cartridge, which obviates for practical purposes, the above-mentioned limitations.

According to an embodiment of the invention, a cartridge for containing a fluid and for use with an electronic delivery device, includes a cartridge housing for holding the fluid, and information providing means. The information providing means is coupled to the cartridge housing to operatively couple with the electronic delivery device to provide predetermined information regarding the cartridge to the electronic delivery device.

In particular embodiments, the information providing means is a set of wires and contacts that provide the predetermined information to electronic delivery device by producing a binary code. In other embodiments, the information providing means is a set of wires and contact bands that provide the predetermined information to electronic delivery device by producing a binary code. In still other embodiments, the information providing means is a bar code that provides the predetermined information to electronic delivery device by reading of the bar code. In further embodiments, the information providing means is disposed on an exterior surface of the cartridge housing.

In preferred embodiments, the predetermined information provided by the information providing means includes information selected from the group of information including, but not limited to, correct insertion, correct orientation, type of fluid contained in the cartridge housing, expiration date of the fluid in the cartridge housing, and maximum dosage of the fluid in the cartridge housing. Also, preferably, the electronic delivery device is an electronic pen-type injector, the cartridge is a medication cartridge, and the fluid is a medication.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 6:
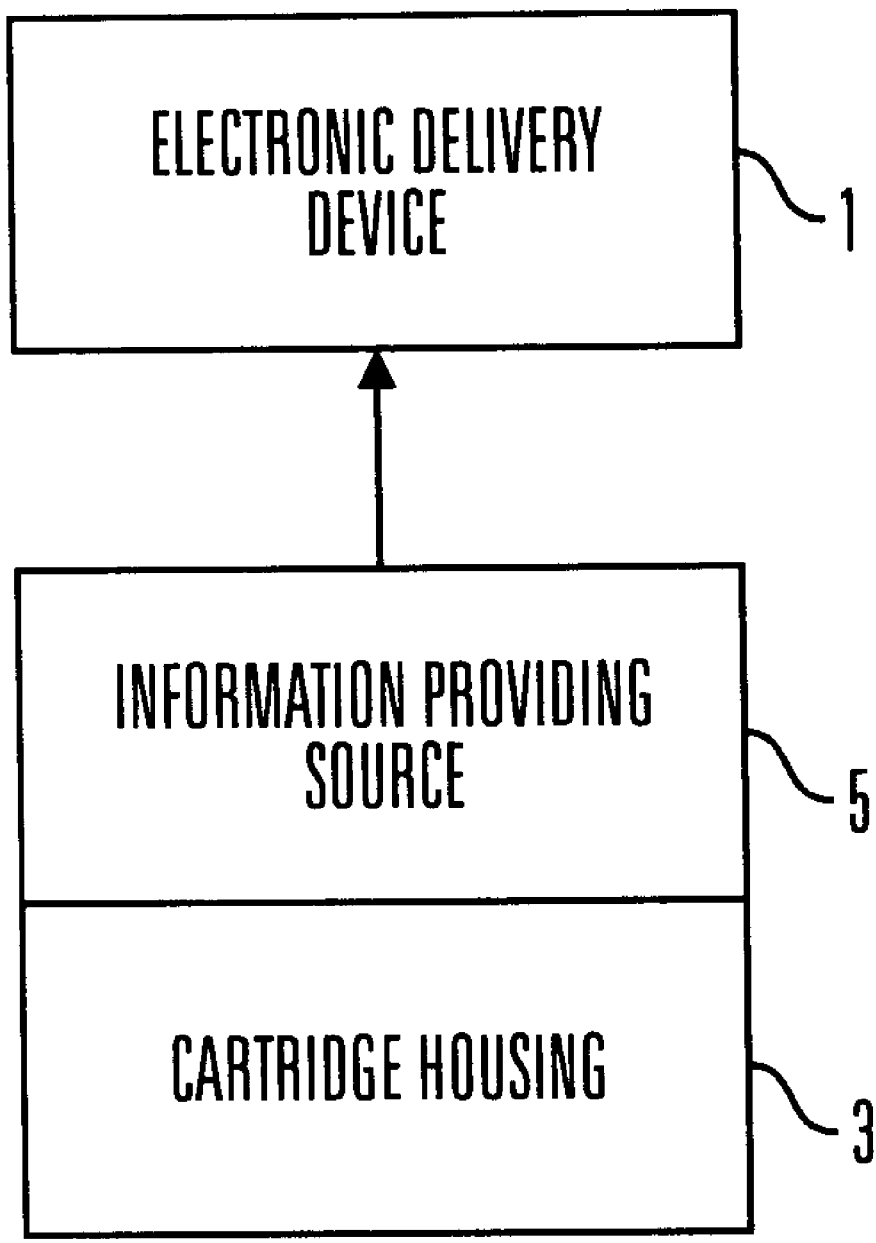
FIG. 6 is a simplified block diagram of a medication cartridge in accordance with an embodiment held in an electronic delivery device.

As shown in the drawings for purposes of illustration, the invention is embodied in a medication cartridge. In preferred embodiments of the present invention, the medication cartridge is used for an injection with an electronic pen-type injector and then discarded. Typical electronic pen-type injectors are shown and described in U.S. Pat. No. 5,593,390, issued Jan. 14, 1997 to Castellano et al., which is herein incorporated by reference. However, it will be recognized that further embodiments of the present invention may be used with other types of electronic invasive delivery or transfer devices, such as IV drip systems, infusion pumps or the like, for delivering substances into the body (see FIG. 6, which shows an electronic delivery device 1 coupled to a cartridge housing 3 including an information providing source 5 that is operatively coupled to the electronic delivery device 1 to provide predetermined information to the electronic delivery device 1). In still further embodiments, the medication cartridges may be used to deliver other medical substances such as vitamins, hormones, vaccines, antibiotics or other medications, or may deliver other liquid substances, such as dyes, tracers or the like.

Embodiments of this present invention are directed to an improved medication cartridge for use with the electronic pen-type injectors, infusion pumps, electronic delivery devices and/or combination devices that include a characteristic monitor. The medication cartridges include some circuitry or indicia applied to the exterior of the medication cartridge that will allow the electronic pen-type injectors, infusion pumps and/or electronic delivery devices to determine characteristics about the medication cartridge and the medication (or liquids) contained in the medication cartridge. Some embodiments provide a minimum of information and would be relatively inexpensive to implement, while others may utilize complex circuitry to provide very detailed information about the medication cartridge. In preferred embodiments, the improved medication cartridge uses existing glass or plastic medication cartridge specifications and dimensions to minimize FDA certification requirements. However, in alternative embodiments, the improved medication cartridges may be made out of other materials, such as composites, metals, ceramics or the like, and may be made to other dimensions and specifications to suit specific needs of the users and the electronic pen-type injectors, infusion pumps and/or electronic delivery devices.

Figure 2:
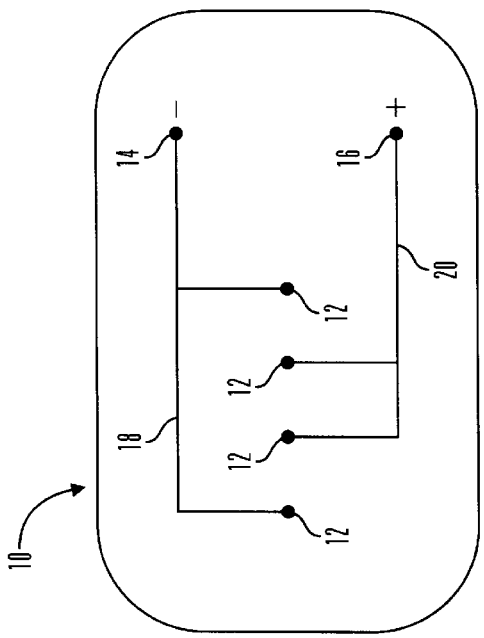
FIG. 2 is an enlarged schematic of the medication cartridge shown in FIG. 1.
Figure 1:
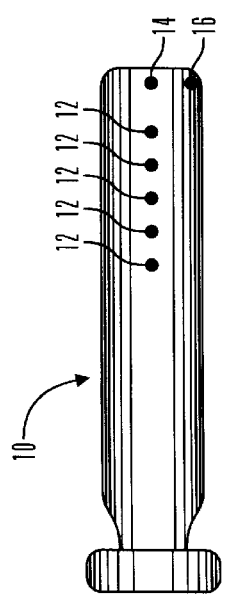
FIG. 1 is a side view of a medication cartridge in accordance with a first embodiment of the present invention.

A medication cartridge 10 in accordance with a first embodiment of the present invention is shown in FIGS. 1 and 2. The cartridge 10 includes a plurality of contacts 12 that mate with corresponding contacts on the electronic pen-type injector, infusion pump and/or electronic delivery device (see FIG. 6). The contacts 12 are connected to either a ground contact 14 or a positive contact 16 through corresponding wires 18 and 20. The electronic pen-type injector, infusion pump and/or electronic delivery device supplies the ground and positive values to the corresponding contacts 14 and 16. The electronic pen-type injector, infusion pump and/or electronic delivery device then reads the resulting value from the contacts 12, which produce information or a binary input that can be indicative of medication type (e.g., types of insulin), expiration date, the amount of medication contained in the cartridge, the maker of the medication, proper insertion of the medication cartridge 10, a maximum dosage or the like. This information can then be displayed on the electronic pen-type injector, infusion pump and/or electronic delivery device or used to control the electronic pen-type injector, infusion pump and/or electronic delivery device to improve performance (e.g., warn of exceeding maximum dosage or of improper insertion into the electronic pen-type injector). The embodiment of FIGS. 1 and 2 uses spot contacts 12, 14 and 16 with the wires 18 and 20 insulated or covered with opaque plastic. This embodiment requires angular alignment of the medication cartridge 10 to the proper angular orientation in the electronic pen-type injector, infusion pump and/or electronic delivery device to read the information from the medication cartridge 10. The contacts 12, 14 and 16, and wires 18 and 20, may be formed from metal tape, vapor deposition or printed circuit board techniques. If tight tolerances can be maintained, the contacts may only take up a small portion of the surface area of the medication cartridge 10.

Figure 4:
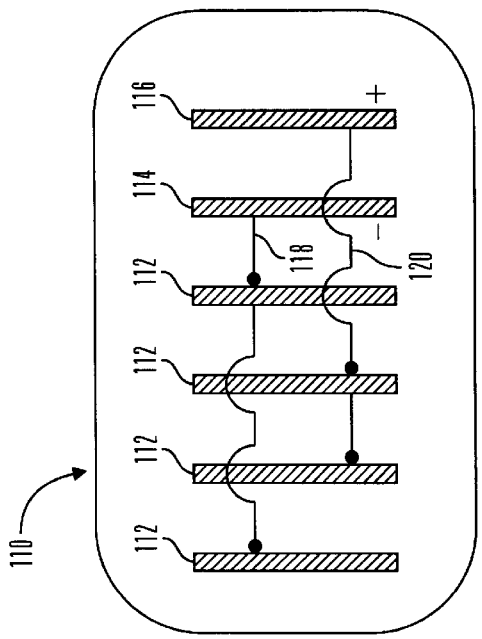
FIG. 4 is an enlarged schematic of the medication cartridge shown in FIG. 3.
Figure 3:
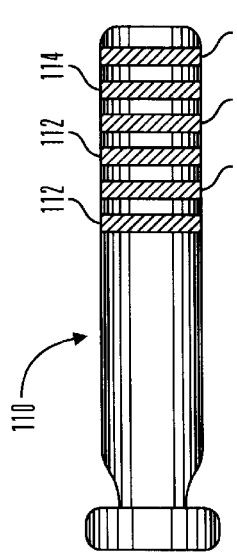
FIG. 3 is a side view of a medication cartridge in accordance with a second embodiment of the present invention.

FIGS. 3 and 4 illustrate a medication cartridge 110 in accordance with a second embodiment of the present invention. The medication cartridge 110 uses contact bands 112, 114 and 116, instead of the spot contacts 12, 14 and 16, that perform in a manner similar to the contacts 12, 14 and 16 described above. The use of contact bands 112, 114 and 116 avoids the necessity of orientating the angle of the medication cartridge 110 to insure that the electronic pen-type injector can obtain the information from the medication cartridge 110. The bands 112, 114 and 116 are connected together by the use of corresponding wire leads 118 and 120 that are in electrical contact with specific bands to generate information that is used by the electronic pen-type injector, infusion pump and/or electronic delivery device. In further embodiments, the contact bands 112, 114 and 116 need only substantially encircle the medication cartridge 110 such that a small break in the substantially encircling contact bands will still permit the medication cartridge 110 to be placed within an electronic delivery device in any orientation and still be readable by the electronic delivery device. For instance, there will still be sufficient electrical contact with the contact bands regardless of orientation of the medication cartridge 110 to permit reading of the information represented by the contact bands.

The above two embodiments shown in FIGS. 1–4 may be applied to an end of the medication cartridges as an adhesive label that contains the required contacts and wires. This would simplify manufacturing and reduce costs. These embodiments are also probably the least expensive to implement from an electronic pen-type injector, infusion pump and/or electronic delivery device manufacturing standpoint and only moderately add to the cost for production of the medication cartridges, since the contacts have to be applied to the cartridges either during production or afterward by application of an adhesive label.

Figure 5:
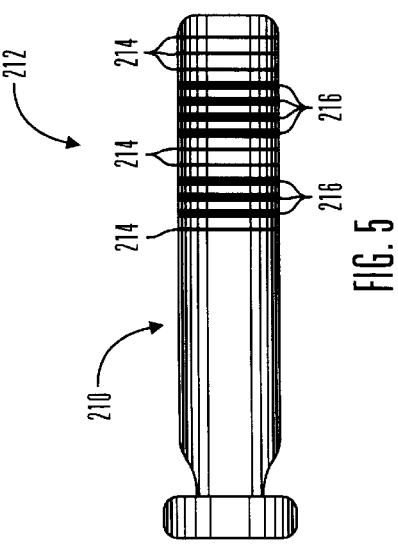
FIG. 5 is a side view of a medication cartridge in accordance with a third embodiment of the present invention.

FIG. 5 illustrates a medication cartridge 210 in accordance with a third embodiment of the present invention. This medication cartridge 210 uses a bar code 212 formed from thin lines 214 and thick lines 216 that are read by a small optical scanner (not shown) in the electronic pen-type injector to obtain the information. The bar code 212 can be either a narrow width that requires angular orientation of the medication cartridge 210 or the bar code 212 lines can completely encircle the medication cartridge 210. The bar code 212 may be applied using the same techniques currently used to apply labeling to the cartridges or the bar code 212 may be applied by a label. This embodiment is probably the least expensive from a medication cartridge manufacturing standpoint, since labels are already printed onto the medication cartridges. However, this would increase the cost of the electronic pen-type injector, infusion pump and/or electronic delivery device, since a small optical scanner would now be required. In a further embodiment, the cartridge has a magnetic strip or code applied to the cartridge, which is then read by a magnetic scanner in the electronic pen-type injector, infusion pump and/or electronic delivery device. In further embodiments, the bar code 212 need only substantially encircle the medication cartridge 210 such that a small break in the substantially encircling bar code will still permit the medication cartridge 210 to be placed within an electronic delivery device in any orientation and still be readable by the electronic delivery device. For instance, there will still be sufficient readable contact (such as sufficiently covering an optical reader or the like) with the bar code 212 regardless of orientation of the medication cartridge 210 to permit reading of the information represented by the bands. In particular embodiments, the bar code utilizes standard wide and narrow lines. In further embodiments, the bar code an use lines of a fixed width and their presence or absence is handled in a manner similar to that described above in the embodiment of FIGS. 3 and 4. In other embodiments, two or more lines are needed to provide the information.

Although the illustrated embodiments describe the wires and bar codes being disposed on the exterior of the medication cartridge, it may be possible to place some or all of the elements on the interior of the medication cartridge or within the material forming the medication cartridge. This would improve the durability of the various embodiments; however, this would increase costs, since the medication cartridges and electronic pen-type injectors, infusion pumps and/or electronic delivery devices would likely require FDA re-certification.

Although not illustrated, a further embodiment would employ a microchip that is adhesively applied to the medication cartridge, and which is then coupled to the electronic pen-type injector, infusion pump and/or electronic delivery device when the medication cartridge is inserted in the electronic pen-type injector, infusion pump and/or electronic delivery device. This would permit infusion pump and/or electronic delivery device (not shown) so that the contact strip or the like is inserted independently to indicate the information for the entire box of cartridges. Although this would reduce costs and minimize any impact on manufacturing of the cartridges, it looses some of the advantages of independent labeling, since a user may forget to change the insert when using cartridges from different boxes.

Advantages to these embodiments are improved control of dosing and more information for the electronic pen-type injector, infusion pump and/or electronic delivery device to better report patient progress.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A cartridge for containing a fluid and for use with an electronic delivery device, the cartridge comprising:
    a cartridge housing for holding the fluid; and
    an information providing source coupled to the cartridge housing to operatively couple with the electronic delivery device for providing predetermined information, independent of an administered dosage, regarding the cartridge to the electronic delivery device, wherein the information providing source includes at least one ring of material that substantially encircles the cartridge housing.

2. A cartridge according to claim 1, wherein the information providing source is a set of wires and the at least one ring of material are contact bands that provide the predetermined information to electronic delivery device by producing a binary code.

3. A cartridge according to claim 1, wherein the at least one ring of material of the information providing source is a bar code that provides the predetermined information to electronic delivery device by reading of the bar code.

4. A cartridge according to claim 1, wherein the information providing source is disposed entirely on an exterior surface of the cartridge housing.

5. A cartridge according to claim 1, wherein the predetermined information from the information providing source includes information selected from the group consisting essentially of correct insertion, correct orientation, type of fluid contained in the cartridge housing, expiration date of the fluid in the cartridge housing, and maximum dosage of the fluid in the cartridge housing.

6. A cartridge according to claim 1, wherein the electronic delivery device is an electronic pen-type injector, wherein the cartridge is a medication cartridge, and wherein the fluid is a medication.

7. A cartridge according to claim 1, wherein the electronic delivery device is an infusion pump, wherein the cartridge is a medication cartridge, and wherein the fluid is a medication.

8. A cartridge according to claim 1, wherein the at least one ring of material of the information providing source is two ore more rings of material.

9. A cartridge according to claim 1, wherein the at least one ring of material of the information providing source permits operative coupling to the electronic delivery device independent of angular orientation.

10. A system utilizing a cartridge for containing a fluid, the system comprising:
    an electronic delivery device;
    a cartridge housing for holding the fluid configured to be coupled to the electronic and to provide predetermined information to the electronic delivery device; and
    an information providing source coupled to the cartridge housing to operatively couple with the electronic delivery device for providing the predetermined information, independent of an administered dosage, regarding the cartridge to the electronic delivery device, wherein the information providing source includes at least one ring of material that substantially encircles the cartridge housing.

11. A system according to claim 10, wherein the information providing source is a set of wires and the at least one ring of material are contact bands, disposed on an exterior surface of the cartridge housing, that provide the predetermined information to electronic delivery device by producing a binary code.

12. A system according to claim 10, wherein the at least one ring of material of the information providing source is a bar code, disposed on an exterior surface of the cartridge housing, that provides the predetermined information to electronic delivery device by reading of the bar code.

13. A system according to claim 10, wherein the information providing source is disposed entirely on an exterior surface of the cartridge housing.

14. A system according to claim 10, wherein the predetermined information from the information providing source includes information selected from the group consisting essentially of correct insertion, correct orientation, type of fluid contained in the cartridge housing, expiration date of the fluid in the cartridge housing, and maximum dosage of the fluid in the cartridge housing.

15. A system according to claim 10, wherein the electronic delivery device is an electronic pen-type injector, wherein the cartridge is a medication cartridge, and wherein the fluid is a medication.

16. A system according to claim 10, wherein the electronic delivery device is an infusion pump, wherein the cartridge is a medication cartridge, and wherein the fluid is a medication.

17. A system according to claim 10, wherein the at least one ring of material of the information providing source is two ore more rings of material.

18. A system according to claim 10, wherein the at least one ring of material of the information providing source permits operative coupling to the electronic delivery device independent of angular orientation.

* * * * *